United States Patent
Ganzoni

(10) Patent No.: US 7,841,215 B2
(45) Date of Patent: Nov. 30, 2010

(54) KNITTED BANDAGE

(75) Inventor: Stefan Ganzoni, Bottmingen (CH)

(73) Assignee: Ganzoni Management AG (CH)

( * ) Notice: Subject to any disclaimer, the term of this patent is extended or adjusted under 35 U.S.C. 154(b) by 150 days.

(21) Appl. No.: 12/065,869

(22) PCT Filed: Jun. 29, 2006

(86) PCT No.: PCT/CH2006/000468

§ 371 (c)(1), (2), (4) Date: Mar. 18, 2008

(87) PCT Pub. No.: WO2007/028263

PCT Pub. Date: Mar. 15, 2007

(65) Prior Publication Data

US 2008/0195019 A1     Aug. 14, 2008

(51) Int. Cl.
    D04B 7/12         (2006.01)
(52) U.S. Cl. .................................................... 66/192
(58) Field of Classification Search .................. 66/202, 66/170, 171, 178 R, 178 A
    See application file for complete search history.

(56) References Cited

U.S. PATENT DOCUMENTS

| | | | |
|---|---|---|---|
| 2,574,737 A * | 11/1951 | Goodchild | 66/178 A |
| 2,902,819 A * | 9/1959 | Ross | 57/225 |
| 3,306,288 A * | 2/1967 | Rosenfield | 602/60 |
| 4,470,250 A | 9/1984 | Arenz et al. | |
| 5,133,199 A * | 7/1992 | Parikh et al. | 66/192 |
| 5,256,134 A * | 10/1993 | Ingham | 602/8 |
| 7,043,329 B2 * | 5/2006 | Dias et al. | 700/141 |
| 7,134,265 B2 * | 11/2006 | Shigemura | 57/225 |

FOREIGN PATENT DOCUMENTS

| | | |
|---|---|---|
| DE | GB 983 719 | 2/1965 |
| DE | GB 2 104 558 | 3/1983 |
| EP | 0161572 A1 | 11/1985 |
| EP | 0 818 567 | 1/1998 |
| EP | 0818567 A1 | 1/1998 |
| FR | 2 654 925 | 11/1989 |
| FR | 2 654 925 | 5/1991 |
| FR | 2 789 301 | 2/1999 |
| FR | 2 789 301 | 8/2000 |
| FR | 2 848 541 | 12/2002 |
| GB | 983 719 | 2/1965 |

(Continued)

OTHER PUBLICATIONS

Office Action dated Jun. 3, 2008 issued in parallel European Application No. 05 019 288.9.

(Continued)

*Primary Examiner*—Danny Worrell
(74) *Attorney, Agent, or Firm*—Ostrolenk Faber LLP

(57) ABSTRACT

A medical bandage consists of a knit fabric made from loop yarns without inlaid yarns. The loop yarns are multifilament yarns having at least one elastic filament, a plurality of synthetic microfilaments and a plurality of cellulose or cellulosic filaments. The bandage has a linear and a non-linear stretching regime, with an operating point lying between them. When it is applied to a patient, it is elastically stretched to the operating point, which allows to generate reproducible, well defined compression forces.

12 Claims, 2 Drawing Sheets

FOREIGN PATENT DOCUMENTS

| | | |
|---|---|---|
| GB | 1078440 | 8/1967 |
| GB | 2 104 558 | 3/1983 |

OTHER PUBLICATIONS

Office Action dated Mar. 19, 2009 from the European Patent Office in EP Application No. 05 019 288.9.

International Search Report of PCT/CH2006/000468.
European Search Report of EP 05019288.9.
International Search Report dated Dec. 12, 2006 issued in corresponding Int'l Application No. PCT/CH2006/000468.
Excerpt from Christine Moffatt, "Compression Therapy in Practice," Wounds Publishing, United Kingdom, p. 40, 2007.
Excerpt from Thuasne magazine, 1 page, Nov. 10, 2008.

\* cited by examiner

KNITTED BANDAGE

CROSS REFERENCE TO RELATED APPLICATIONS

The present application is a 35 U.S.C. §§371 national phase conversion of PCT/CH2006/000468, filed Jun. 29, 2006, which claims priority of European Application No. 05 019 288.9, filed Sep. 6, 2005, the disclosures of which have been incorporated herein by reference. The PCT International Application was published in the English language.

TECHNICAL FIELD

The invention relates to a medical bandage.

BACKGROUND ART

Conventional medical bandages are classified in three categories, according to their stretch properties:

a) Non-elastic bandages (bandages that are substantially fixed in length and cannot be stretched);

b1) Short stretch bandages (bandages that can be extended by approximately 70% of length by stretching);

b2) Long stretch bandages (bandages that can be extended by 150% of length or more by stretching).

Non-elastic bandages can be used to prevent a limb from swelling, while elastic bandages are primarily used for compression purposes.

Medical bandages are used in place of compression stockings when the limb dimensions are very unusual and standard medical compression stockings cannot fit properly. They have, however, the following disadvantages:

When non-elastic bandages are used and a limb's swelling is resorbed, the bandage loses its effect; and When stretch bandages are used, the level of applied compression is related to the degree of stretching of the bandage, and this degree is hard to control when applying the bandage.

Hence, the amount of compression generated by a bandage is hard to control.

DISCLOSURE OF THE INVENTION

The goal of the present invention is therefore to provide a bandage that allows a better control of the applied pressure.

This goal is met by the bandage disclosed and claimed herein.

Accordingly, the bandage is formed by a knit fabric without inlaid yarns. In other words, the fabric comprises loop yarns but no inlaid yarns. The loop yarns are multifilament yarns comprising at least one first filament and a plurality of second filaments. The first filament has higher elasticity (i.e. can be stretched more easily) than the second filaments. In the relaxed state, the first filament is shorter than the second filaments. Hence the first filament tends to contract the thread to a length where the second filaments have excess length and e.g. form small loose loops. When the thread is stretched, the first filament is elastically extended and the second filaments are straightened. Once the second filaments are fully straightened, the yarn becomes harder to stretch and then the bandage acquires the mechanical properties of a non-elastic bandage.

A bandage of this type can be stretched in both directions, i.e. along the bandage and perpendicular thereto. Stretching is easy while the second filaments are not yet fully straightened and becomes much harder once they are. The transition between the two stretching regimes is, in the following, called the bandage's "operation point".

When applying the bandage to a limb, the user can stretch it to the operation point, which is fairly easy to find and provides a predefined compression. When the limb's swelling reduces, the resulting change of force is comparatively small.

BRIEF DESCRIPTION OF THE DRAWINGS

Further advantageous embodiments are described in the dependent claims as well as in the following description, which makes reference to the annexed drawings. The drawings show:

MODES FOR CARRYING OUT THE INVENTION

Figure 1:
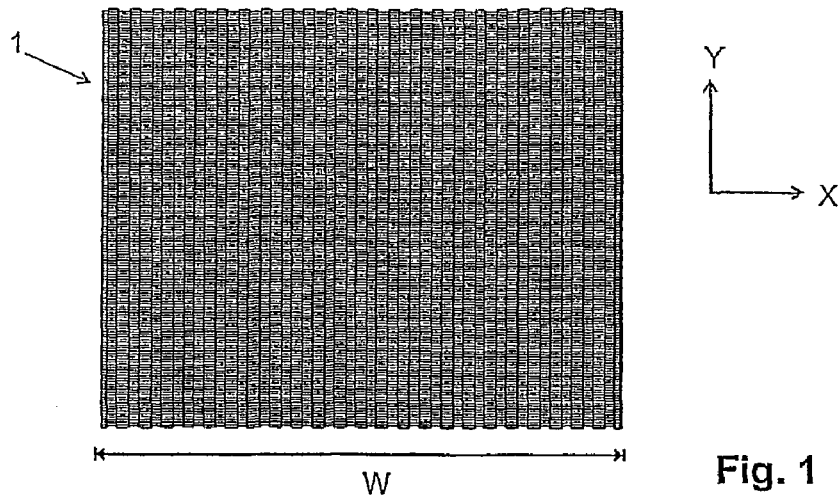
FIG. 1 a section of a bandage.

The section of bandage 1 shown in FIG. 1 extends along a longitudinal direction Y (the vertical direction in FIG. 1) and has a width W. The loop yarns forming the bandage run generally along a transverse direction X perpendicular to the longitudinal direction Y.

Figure 2:
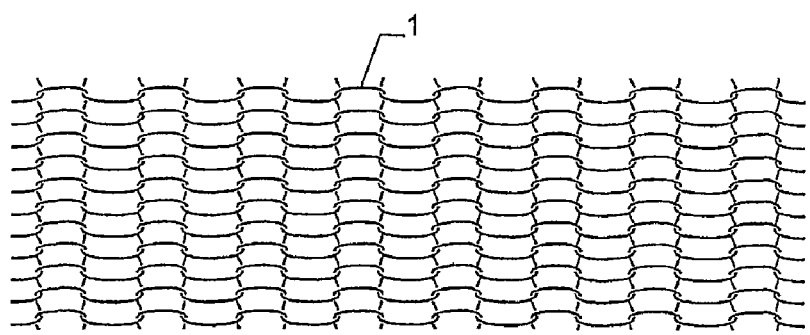
FIG. 2 a more detailed view of the knit.

Substantially all yarns used in the fabric of the bandage are loop yarns 2 knitted advantageously in a plain stitch ("Jersey stitch") as depicted in FIG. 2.

Each yarn advantageously consists of three constituent types of filaments:

a) It comprises at least a first, elastic filament. This filament can be elastically extended by at least 30% in length, advantageously by at least 50% in length. It is formed by a synthetic, elastic yarn, such as an elastan. Examples are Lycra (Dupont), Creora (Hyosung), or Dorlastan (Bayer). The first filament has a specific weight of 22 to 78 dtex. Preferable weights are 22, 44 or 78 dtex, depending on desired elastic modulus (i.e. elastic constant slope below the operating point, see below) of the bandage. The first filament provides the yarn with its elasticity as described below.

b) It further comprises a plurality of second filaments of cellulose and/or a cellulosic material, such as fibers of cotton, viscose, or lyocell. The second filaments cumulatively have a (metric) yarn number of 224-110 Nm, advantageously 159 Nm. The purpose of the second filaments is to provide comfort to the wearer. Cotton is the most advantageous material to be used for the second filaments. The second filaments have poorer elasticity (i.e. are harder to extend) than the first filament, i.e. it takes more force per percent of extension to extend (all) the second filaments than to extend the first filament(s).

c) Finally, it comprises a plurality of third filaments of a synthetic material, such as of polyamide, polyester and/or polypropylene. The third filaments have a total specific weight of 22 to 156 dtex, i.e. the cumulated specific weight of all third filaments is 22 to 156 dtex. An advantageous weight is 44 dtex. Their purpose is primarily to provide bulk to the yarn (as it is also a secondary purpose of the second filaments), while they are more durable than the second filaments. Again, the third filaments have poorer elasticity (i.e. are harder to extend) than the first filament.

The loop yarns are e.g. manufactured by an air-jet intermingling process as described in EP 0 818 567 A1. In such a yarn, the first filament (the elastic filament) is joined to the other filaments while it is in a stretched state, e.g. by being extended in length by 30%. In other words, when the first filament is released to its relaxed state, it is shorter than the second and third filaments and the latter form bends and loops to adjust for this difference. The technique of yarn combination could also be a conventional covering process involving an elastic filament as core yarn and the second and third filaments as covering components. The three components could also be placed side by side in a parallel manner at the knitting process.

Figure 3:
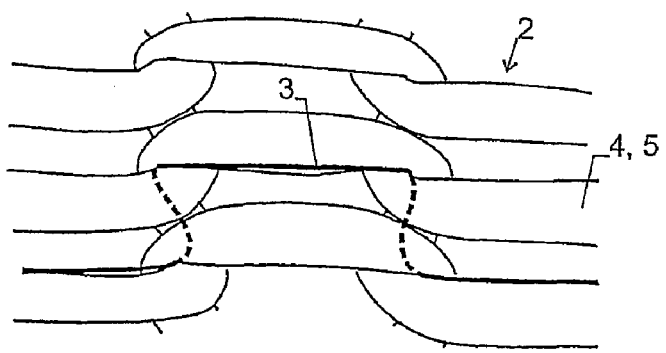
FIG. 3 a close view of the knitted yarns.

The bandage is manufactured by knitting the loop yarns while they are elastically stretched by e.g. at least 30% in length. When released, the loop yarns relax into a structure as shown in FIG. 3, where adjacent yarns come into contact with each other. In FIG. 3, the first, elastic filament 3 of one of the yarns is depicted as a thick line, while the second and third filaments 4, 5 loosely form the bulk of the yarns.

The bandage can be stretched elastically along the longitudinal direction Y as well as the transverse direction X. The stretchability in the X direction allows the performance of the bandaging process on an anatomic limb shape which is not similar to a cylinder. The loop yarns 2 are advantageously arranged in a plain stitch arrangement because this type of stitch allows similar extension of the fabric in both directions. Alternatively, other types of stitches can be used as well, such as a floated stitch or a tuck stitch if a stiffer elasticity modulus is required while using the same size of yarn.

When the fabric is being stretched, the loop yarns are first extended by elastically stretching the first filament and straightening the second and third filaments. In this region, the fabric's response is linear elastic, i.e. the extension is basically proportional to the applied force. Once the second and third filaments are straightened, further extension of the fabric is only possible by applying a much stronger force, i.e. a non-linear elastic region is entered.

Figure 4:
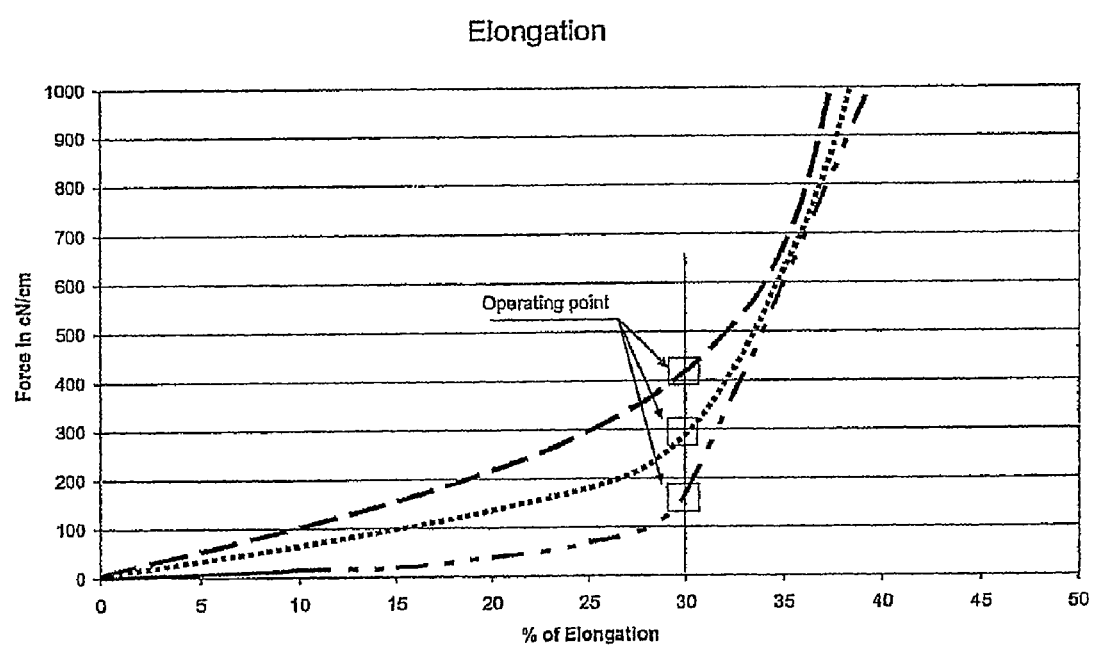
FIG. 4 the elongation of the fabric as a function of applied force per width.

This behavior is depicted in FIG. 4 for three fabrics that differ by the weight of the first filament, the bottommost curve belonging to a fabric where the first filament has a specific weight of 22 dtex, the middle curve belonging to a fabric with a first filament of a specific weight of 44 dtex and the topmost curve belonging to a fabric with a first filament of a specific weight of 78 dtex.

In the shown embodiment, the extension where the linear elastic region ends before the non-linear elastic region starts (the "operating point" of the bandage) lies at approximately 30% elongation. When applying the bandage to the limb, the fabric should be stretched approximately to this operating point as described above. Stretching can be carried out manually or, more conveniently, by means of a pre-stretching device, such as described in FR 2 848 541.

While there are shown and described presently preferred embodiments of the invention, it is to be distinctly understood that the invention is not limited thereto but may be otherwise variously embodied and practiced within the scope of the following claims.

The invention claimed is:

1. A medical bandage, wherein said bandage is formed by a knit fabric of loop yarns without inlaid yarns, wherein said loop yarns are multifilament yarns, each loop yarn comprising at least one first filament and a plurality of second filaments, wherein said first filament has higher elasticity than said second filaments and wherein, in a relaxed state of said first filament, said first filament is shorter than said second filaments,
wherein said second filaments are of cellulose and/or a cellulosic material;
wherein said loop yarns further comprise a plurality of third, synthetic filaments; and
wherein said bandage is configured to be extended in a linear elastic manner from a relaxed position by approximately 30 percent in length until it reaches a non-linear elastic condition.

2. The medical bandage of claim 1 wherein said second filaments are cotton filaments.

3. The medical bandage of claim 1 wherein said third filaments are selected from the group of materials consisting of polyamide, polyester and polypropylene.

4. The medical bandage of claim 1 wherein said third, synthetic filaments have a total specific weight of 22 to 156 dtex.

5. The medical bandage of claim 1 wherein, in a relaxed state of said first filament, said first filament is shorter than said third filaments.

6. The medical bandage of claim 1 wherein said first filament has a total specific weight of 22 to 78 dtex.

7. The medical bandage of claim 1 wherein said second filament has a yarn number between 110 and 224 Nm.

8. The medical bandage of claim 1 wherein said loop yarns are arranged in a plain stitch.

9. The medical bandage of claim 1 wherein said loop yarns are arranged in a floated stitch or tuck stitch.

10. The medical bandage of claim 1 wherein said loop yarns run along a direction perpendicular to a longitudinal direction of the bandage.

11. A method for manufacturing a bandage comprising:
providing a knit fabric of loop yarns without inlaid yarns, wherein said loop yarns are multifilament yarns, each loop yarn comprising at least one first filament and a plurality of second filaments, wherein said first filament has higher elasticity than said second filaments and wherein, in a relaxed state of said first filament, said first filament is shorter than said second filaments; and
further comprising the step of knitting said loop yarns while said loop yarns are elastically stretched by at least 30% in length.

12. A medical bandage, wherein said bandage is formed by a knit fabric of loop yarns without inlaid yarns, wherein said loop yarns are multifilament yarns, each loop yarn comprising at least one first filament and a plurality of second filaments, wherein said first filament has higher elasticity than said second filaments and wherein, in a relaxed state of said first filament, said first filament is shorter than said second filaments, the medical bandage being configured to be extended by approximately 30% in length when applying the medical bandage to a limb of a user, the extension of the medical bandage by approximately 30% in length being at the end of the linear elastic region of the extension of the medical bandage.

* * * * *